United States Patent
Paschalis

(10) Patent No.: US 11,026,778 B2
(45) Date of Patent: Jun. 8, 2021

(54) KERATOPROSTHESIS APPARATUSES, SYSTEMS, AND METHODS

(71) Applicant: Massachusetts Eye and Ear Infirmary, Boston, MA (US)

(72) Inventor: Eleftherios Ilios Paschalis, Quincy, MA (US)

(73) Assignee: Massachusetts Eye and Ear Infirmary, Boston, MA (US)

(*) Notice: Subject to any disclaimer, the term of this patent is extended or adjusted under 35 U.S.C. 154(b) by 225 days.

(21) Appl. No.: 16/327,029

(22) PCT Filed: Aug. 24, 2017

(86) PCT No.: PCT/US2017/048462
§ 371 (c)(1),
(2) Date: Feb. 21, 2019

(87) PCT Pub. No.: WO2018/039478
PCT Pub. Date: Mar. 1, 2018

(65) Prior Publication Data
US 2019/0192281 A1 Jun. 27, 2019

Related U.S. Application Data

(60) Provisional application No. 62/378,986, filed on Aug. 24, 2016.

(51) Int. Cl.
*A61F 2/14* (2006.01)
*A61F 2/16* (2006.01)

(52) U.S. Cl.
CPC .............. *A61F 2/142* (2013.01); *A61F 2/16* (2013.01); *A61F 2220/0008* (2013.01)

(58) Field of Classification Search
CPC .... A61F 2/142; A61F 2/16; A61F 2220/0008; A61F 2/145; A61F 2/1451; A61F 2/1648;
(Continued)

(56) References Cited

U.S. PATENT DOCUMENTS

| | | |
|---|---|---|
| 4,249,272 A | 2/1981 | Poler |
| 4,470,159 A | 9/1984 | Peyman |

(Continued)

OTHER PUBLICATIONS

International Preliminary Report on Patentability in International Application No. PCT/US2017/048462, dated Feb. 26, 2019, 6 pages.

(Continued)

*Primary Examiner* — Paul B Prebilic
(74) *Attorney, Agent, or Firm* — Fish & Richardson P.C.

(57) ABSTRACT

The present disclosure relates to keratoprosthesis apparatuses comprising a flexible backplate and methods of manufacturing and implanting the new keratoprosthesis apparatuses. The keratoprosthesis apparatuses include a circular backplate composed, at least in part, of a titanium alloy. The circular backplate includes an annular rim portion having a central aperture extending therethrough. A plurality of tabs is positioned along the annular rim portion and extend radially inwardly into the aperture. A plurality of flexible appendages extends radially outwardly from the annular rim portion and is positioned along the annular rim portion at locations corresponding to the plurality of tabs.

18 Claims, 12 Drawing Sheets

(58) Field of Classification Search
CPC ...... A61F 2210/0014; A61F 2220/0025; A61F 2230/0065; A61F 2250/0039; A61F 2250/006; A61F 2250/0062; A61F 2250/0091
See application file for complete search history.

(56) References Cited

U.S. PATENT DOCUMENTS

| | | | | |
|---|---|---|---|---|
| 5,489,301 | A | * | 2/1996 | Barber .................. A61F 2/142 623/5.11 |
| 5,843,185 | A | * | 12/1998 | Leon Rolden .......... A61F 2/142 623/5.11 |
| 6,106,552 | A | | 8/2000 | Lacombe et al. |
| 6,485,516 | B2 | | 11/2002 | Boehm |
| 7,927,052 | B1 | * | 4/2011 | Varden .................. F16B 39/108 411/221 |
| 2010/0168849 | A1 | | 7/2010 | Azar et al. |
| 2011/0089684 | A1 | * | 4/2011 | Schutte ............... F16L 37/0915 285/305 |
| 2015/0216651 | A1 | * | 8/2015 | Parel ...................... A61F 2/142 623/5.11 |
| 2016/0184084 | A1 | * | 6/2016 | Daphna .................. A61F 2/142 623/5.16 |

OTHER PUBLICATIONS

International Search Report and Written Opinion in International Application No. PCT/US2017/048462, dated Oct. 30, 2017, 10 pages.

\* cited by examiner

KERATOPROSTHESIS APPARATUSES, SYSTEMS, AND METHODS

RELATED APPLICATION

The present application is a § 371 national stage application of International Application No. PCT/US2017/048462, filed on Aug. 24, 2017, which claims priority to U.S. Provisional Patent Application No. 62/378,986, filed on Aug. 24, 2016, entitled "KERATOPROSTHESIS APPARATUSES, SYSTEMS, AND METHODS," which application is incorporated herein by reference in its entirety.

TECHNICAL FIELD

The present application relates generally to the field of keratoprosthesis systems.

BACKGROUND

The Boston Keratoprosthesis is a commonly used artificial cornea that is utilized in a broad array of corneal conditions not amenable to standard corneal transplantation. The Boston Keratoprosthesis artificial cornea device is designed like a collar button, with a plastic stem and a backplate supporting the donor corneal tissue. The Boston Keratoprosthesis is generally implemented with a donor cornea having a central hole to mount the optical stem. The backplate is placed at the posterior surface of the cornea (behind the Descemet membrane and epithelium) and provides mechanical support to the stem and graft. After assembly, the graft cornea is sutured to the host cornea in the same fashion that a penetrating keratoplasty (PK) procedure is performed.

Recent advancements in the Boston Keratoprosthesis artificial cornea devices have allowed the adaptation of titanium as a backplate material, which resulted in marked improvement in retroprosthetic membrane formation and has enhanced the device by providing higher tensile strength, corrosion resistance, bio-inertness, ductility, and lightness (for example, 4.5 g/cm$^3$). However, postoperative complications such as corneal graft melting, necrosis, infection, retroprosthetic membrane, vitritis, endophthalmitis, retinal detachment, and glaucoma remain a reality, especially in patients having autoimmune and chemical burns. The inability of the corneal graft tissue to adhere to a plastic stem formed of a material such as polymethyl methacrylate (PMMA) prevents bio-integration and compromises physical barriers. For example, non-adherence can have an adverse impact on the corneal epithelium and the Descemet membrane by increasing the risk of pathogen entry into the eye. Additionally, a lack of tissue bio-integration prolongs wound healing and promotes low-grade subclinical inflammation, which might have deleterious effects to corneal grafts and the eye. In addition, aqueous leaks through the stem can cause hypotony and retinal detachment, which, if not promptly treated, can result in permanent vision loss.

SUMMARY

The inventors have discovered that a keratoprosthesis apparatus that includes a flexible backplate can be advantageously implanted in the eye without disrupting the corneal endothelium. Some benefits of an intact corneal endothelium include decreased risk of infection, decreased risk of graft failure, and decreased risk of glaucoma. Accordingly, various embodiments disclosed herein provide keratoprosthesis apparatuses and systems having a flexible backplate, and methods of using these apparatuses and systems that can be implanted in the eye without disrupting the corneal endothelium.

Various embodiments provide a keratoprosthesis apparatus including a circular backplate composed, at least in part, of a titanium alloy, wherein the circular backplate includes an annular rim portion having a central aperture extending therethrough, a plurality of tabs positioned along the annular rim portion and extending radially inwardly into the aperture, and a plurality of flexible appendages extending radially outwardly from the annular rim portion and positioned along the annular rim portion at locations corresponding to the plurality of tabs. The plurality of flexible appendages is configured to provide leverage to pivot the plurality of tabs outwardly.

In some implementations, the titanium alloy includes a titanium nickel alloy or a shape memory material such as nitinol.

In some implementations, the titanium alloy includes a super elastic alloy.

In some implementations, the keratoprosthesis apparatuses include an optical stem including a curvilinear crown portion and a neck portion extending from the curvilinear crown portion, wherein the neck portion comprises an annular ridge having a smaller diameter than the neck portion, and wherein the circular backplate is coupled to the optical stem via engagement of the plurality of tabs in the ridge of the neck portion of the optical stem.

In some implementations, the keratoprosthesis apparatuses include a coaxial sleeve positioned about the neck portion of the optical stem. The coaxial sleeve can include a sleeve ridge corresponding to the annular ridge. The circular backplate can be coupled to the optical stem via engagement of the plurality of tabs in the sleeve ridge. The sleeve may be fitted to the optical stem prior to backplate engagement. Alternatively, the backplate can be fitted to the sleeve and then the sleeve with the backplate is fitted to the optical stem as one body.

In some implementations, the sleeve is composed of titanium. In additional implementations, one or more tabs in the plurality of tabs include a curved edge. In some implementations, the circular backplate is configured in a curvilinear profile. In other implementations, the circular backplate is configured for elastic deformation.

In some implementations, an additional plurality of flexible appendages extends radially outwardly from the annular rim portion and is positioned along the annular rim portion at locations intermediate to the plurality of tabs.

Various embodiments provide methods of assembling a keratoprosthesis apparatus. The methods include obtaining a circular backplane having a plurality of tabs positioned along and extending radially inwardly from an annular rim portion of the circular backplate. The plurality of tabs define a space between them The method includes moving the plurality of tabs by flexing a plurality of flexible appendages extending radially outward from the annular rim portion and positioned along the annular rim portion at locations corresponding to the plurality of tabs. This causes the plurality of tabs to pivot about the annular rim portion so as to increase a diameter of the space between the plurality of tabs. The methods include inserting a neck portion of an optical stem including a curvilinear crown portion into the space between the plurality of tabs so as to position an annular ridge in the neck portion having a smaller diameter than the neck portion adjacent the plurality of tabs. The methods can further include releasing the plurality of flexible appendages to reduce the diameter of the space between the plurality of tabs to engage the plurality of tabs in the ridge.

In some implementations, the methods include inserting a sleeve about the neck portion of the optical stem so that the sleeve is positioned on the neck portion between the circular back plate and the neck portion of the optical stem.

Various embodiments provide methods of assembling a keratoprosthesis apparatus. The methods include inserting a neck portion of an optical stem including a curvilinear crown portion into a space between a plurality of tabs positioned along and extending radially inwardly from an annular rim portion of a circular backplate composed of a shape memory alloy and having a plurality of flexible appendages extending radially outward from the annular rim portion and positioned along the annular rim portion so as to position an annular ridge having a smaller diameter than the neck portion adjacent the plurality of tabs; and inwardly flexing the plurality of tabs to reduce a diameter of the space between the plurality of tabs by actuating the shape memory alloy to engage the plurality of tabs in the ridge.

Various embodiments provide a keratoprosthesis apparatus including a circular backplate composed, at least in part, of a titanium alloy. The circular backplate includes an annular rim portion having a central aperture extending therethrough. The keratoprosthesis apparatus includes a plurality of tabs positioned along the annular rim portion and extending radially inwardly into the aperture. The keratoprosthesis apparatuses include a plurality of flexible appendages extending radially outwardly from the annular rim portion and positioned along the annular rim portion. The keratoprosthesis apparatuses include an optical stem including a curvilinear crown portion and a neck portion extending from the curvilinear crown portion. The neck portion includes an annular ridge having a smaller diameter than the neck portion. The circular backplate is coupled to the optical stem via engagement of the plurality of tabs in the ridge of the neck portion of the optical stem.

In some implementations, the appendages include bi-lateral extensions extending from a radially outer end of a flexible appendage in the plurality of flexible appendages.

In some implementations, the bilateral extensions are curvilinear.

In some implementations, the plurality of tabs include a curved edge configured to engage the annular ridge in the neck portion.

All combinations of the foregoing concepts and additional concepts discussed in greater detail below (provided such concepts are not mutually inconsistent) are part of the inventive subject matter disclosed herein. In particular, all combinations of claimed subject matter appearing at the end of this disclosure are part of the inventive subject matter disclosed herein. Terminology explicitly employed herein that also may appear in any disclosure incorporated by reference should be accorded a meaning most consistent with the particular concepts disclosed herein.

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages will be apparent from the following detailed description, and from the claims.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

The features and advantages of the inventive concepts disclosed herein will become more apparent from the detailed description set forth below when taken in conjunction with the drawings.

DETAILED DESCRIPTION

Following below are more detailed descriptions of various concepts related to, and exemplary embodiments of, inventive systems, methods, and components related to a keratoprosthesis.

Deep anterior lamellar keratoplasty (DALK) is a preferred surgical procedure for corneal diseases that do not affect the endothelium. DALK has become a preferred surgical procedure for corneal diseases that do not involve the endothelium and for surgery in patients that do not necessitate full thickness transplantation. The big bubble technique and advancements in microkeratomes/femtosecond lasers have revolutionized DALK surgery and provide distinct advantages over penetrating keratoplasty, such as better wound healing, reduced intraocular inflammation, increased safety, and decreased rejection rate. Various embodiments of the present invention provide a keratoprosthesis apparatus that is suitable for implanting using a DALK technique.

Keratoprostheses

Figure 1:
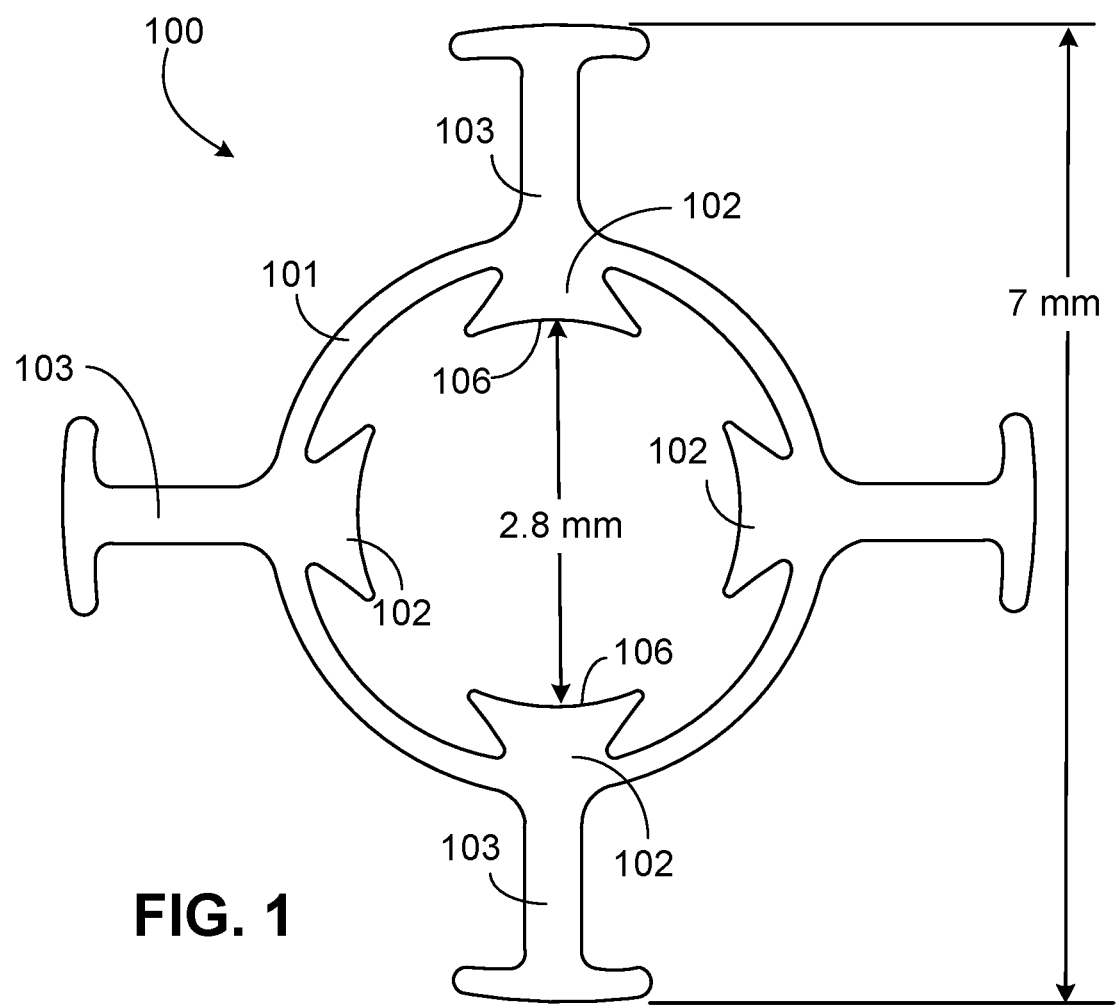
FIG. 1 is a top view of an example of a keratoprosthesis apparatus as described herein.

To achieve this goal various implementations disclosed herein provide a keratoprosthesis apparatus made with a flexible titanium backplate, as shown in FIG. 1 that can be implanted intracorneally in a donor graft using a DALK technique described in further detail in FIGS. 6A-E.

FIG. 1 is a top view of a flexible backplate 100. The flexible backplate is generally composed of a titanium alloy, which can include, but is not limited to, a nickel titanium alloy and/or a nitinol titanium alloy. In some implementations, the flexible backplate is composed of a super elastic alloy. In some implementations, the titanium alloy can include 55% titanium and 45% nickel. In some implementations, the titanium alloy can have a Young's modulus in the range of 20-200 GPa (austenite), 10-100 GPa (martensite). The flexible backplate 100 includes an annular rim portion 101. A plurality of tabs 102 extend radially inward into an optical aperture 105 formed by the annular rim portion 101. The tabs 102 include a curved inner edge 106. As discussed further herein, the inner edge 106 of the tabs 102 is configured for engagement with a round neck portion of an optical stem. The flexible backplate 100 also includes a plurality of flexible appendages 103 that extend radially outward from the annular rim portion 101. The flexible appendages 103 provide support for a donor corneal graft or corneal tissue. The flexible appendages 103 are positioned along the rim a locations corresponding to the tabs 102 so that the flexible appendages 103 can be used as levers to cause the tabs 102 to pivot outward so that a space positioned between the tabs can be varied.

As described in further detail herein, the variation of the space is used for coupling the flexible backplate 100 to an optical stem and in particular to a groove formed in the stem. The position of the tabs may be varied by manually flexing the flexible appendages 103 or by actuating the shape memory of the flexible backplate 100 in implementations where the flexible backplate 100 is composed of a shape memory material. The flexible backplate 100 may be formed into the shape and profile illustrated in FIG. 1 via processes, such as laser cutting, photo etching, and/or stamping.

Figure 2:
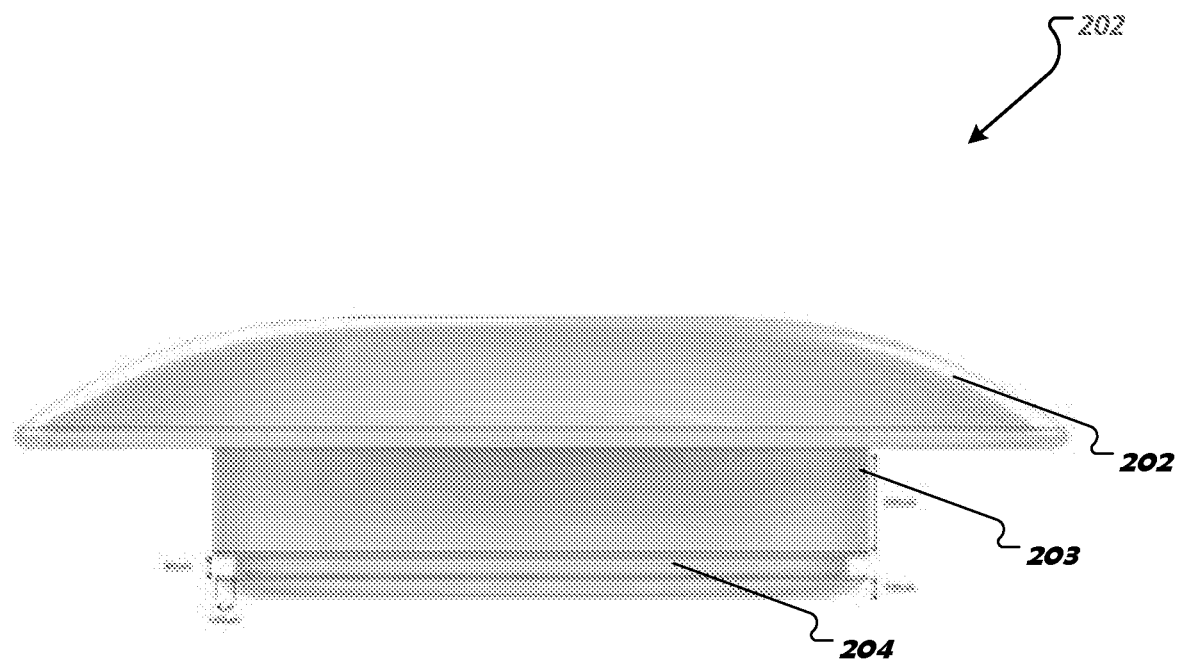
FIG. 2 is a side view of an example of an optical stem as described herein.

FIG. 2 is a side view of an optical stem 202. The optical stem 202 is configured in a manner similar to a collar button. The optical stem 202 can be composed of a plastic material such as polymethyl methacrylate (PMMA) and can be translucent. The optical stem 202 includes a curvilinear crown portion 201 that generally has a larger diameter than a neck portion 203 extending from the crown portion 201. The neck portion 203 is configured to receive a donor corneal graft or corneal tissue having an aperture formed therein. The aperture formed in the donor corneal graft is generally approximately 3 mm in dimeter. Accordingly, the neck portion 203 is also generally approximately 3 mm in dimeter. As discussed further herein, in some embodiments, the neck portion 203 may be fitted with a coaxial titanium sleeve. In such cases, the outer diameter of the combined neck portion 203 and the sleeve substantially correspond to the aperture in the donor corneal graft or corneal tissue. The neck portion 203 includes a groove or annular ridge 204 formed therein. The annular ridge 204 is configured to receive the tabs 102 of the flexible backplate 100 to engage and hold the backplate 100 on the optical stem 202. Accordingly, the annular ridge 204 has a smaller diameter than the neck portion 203. The diameter of the annular ridge 204 generally corresponds to the diameter of a space between the tabs 102, when the tabs 102 are in an unbiased position. The annular ridge 204 is positioned toward a posterior end of the neck portion 203.

Figure 3A:
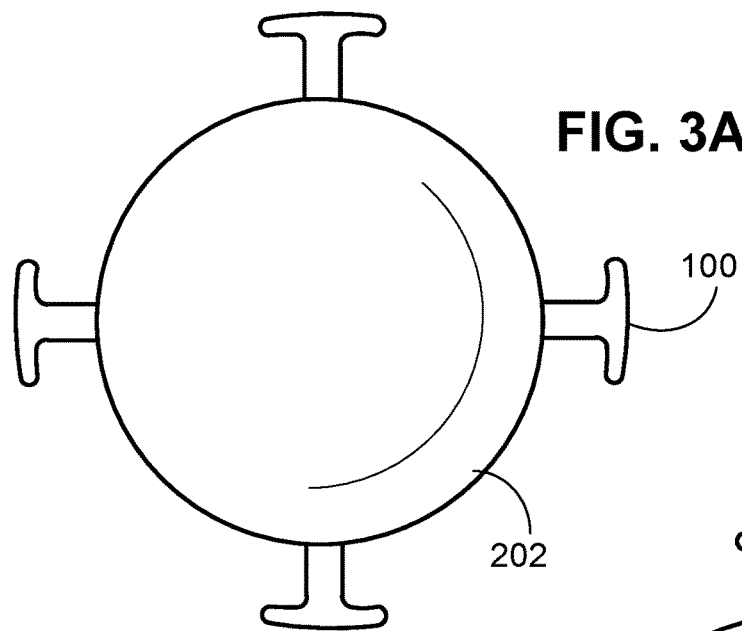
FIGS. 3A-3C are views of the keratoprosthesis apparatus of FIG. 1 coupled to the optical stem of FIG. 2.
Figure 3B:
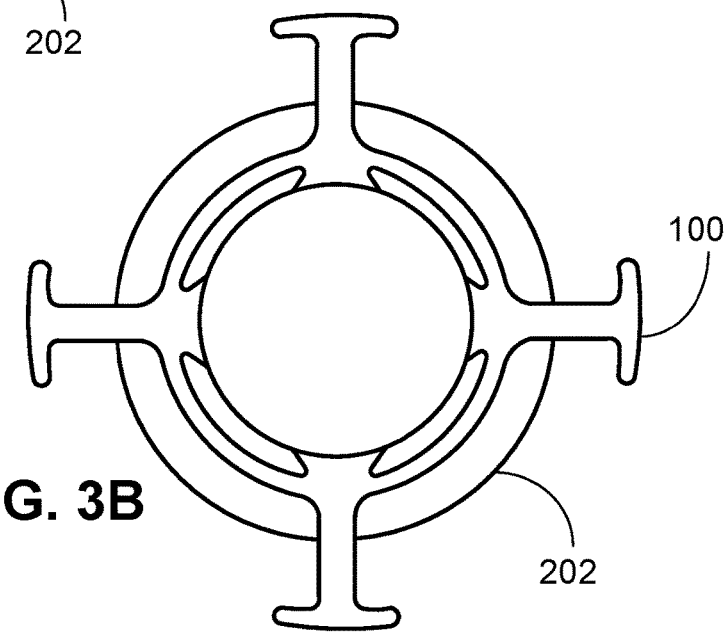
Figure 3C:
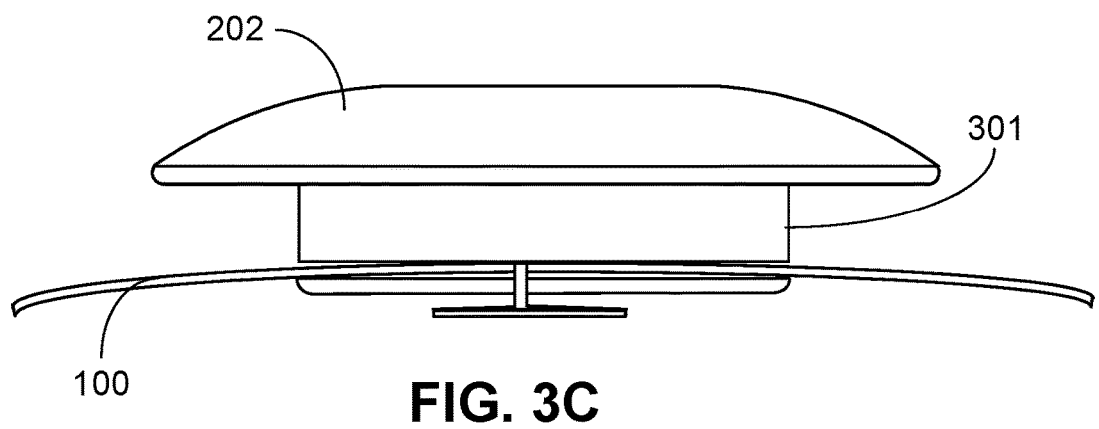

FIGS. 3A-3C are views of a keratoprosthesis apparatus 300 including the flexible backplate 100 of FIG. 1 coupled to the optical stem 202 of FIG. 2. FIG. 3A is a top view. FIG. 3B is a bottom view. FIG. 3C is a side view. As shown in FIG. 3C, the optical stem 202 can be fitted with a titanium sleeve 301 positioned about the neck portion 203 of the optical stem 202. The sleeve 301 is positioned on the neck portion 203 between the flexible back plate 100 and the optical stem 202. As shown in FIG. 3C, the flexible backplate 100 can have a curvilinear profile and can have a radius of curvature including, but not limited to, of 6.8 mm. As described herein, the flexible backplate 100 can be composed of a nitinol material, which can include a super elastic nitinol or a shape memory nitinol. In both materials, the permanent convex shape providing the curvilinear profile is given by high temperature (for example ~540 C) annealing of the nitinol backplate 100 into a mold with the desired curvature. This shape is remembered. In the super elastic nitinol, the material is operated in its austenite phase. The flexible appendages 103 bend and return to the original shape. In the shape memory nitinol, there is a transition temperature between the deformable martensite phase and the flexible austenite phase. In the martensite phase, the shape memory nitinol material will fold and remain folded. Once the temperature exceeds the transformation temperature (for example 35° C.), the nitinol will enter into the austenite phase and become flexible, hence returning to the original shape.

Methods of Making the Keratoprosthesis Described Herein

Figure 4:
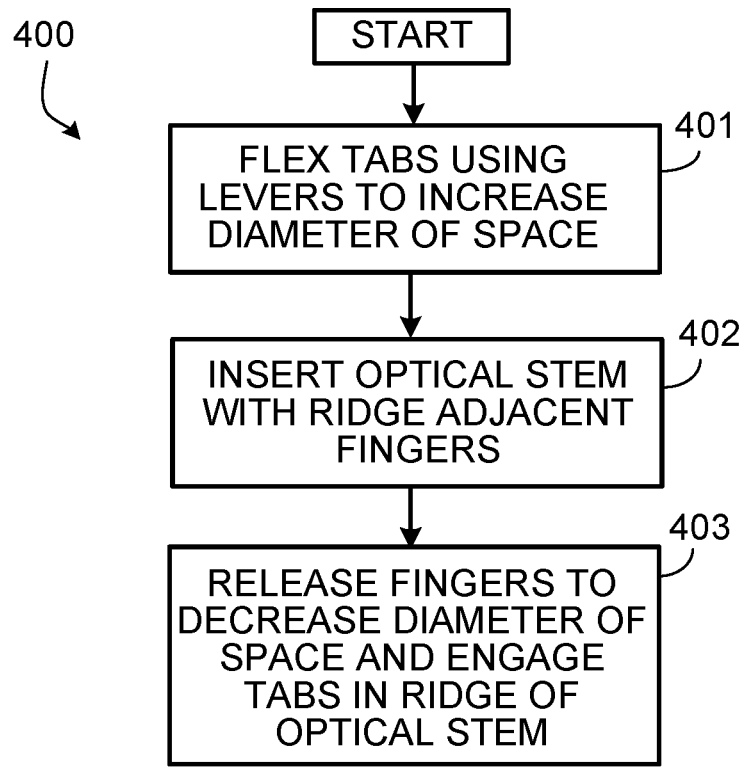
FIG. 4 is a flow diagram of an example of a method of forming a keratoprosthesis apparatus.

FIG. 4 is a flow diagram of a method of forming a keratoprosthesis apparatus. The keratoprosthesis apparatus formed by method 400 may be formed using a flexible backplate 100 composed at least in part, of a titanium alloy. At 401, the flexible backplate 100 is flexed from a first position to a second position. In the first position, the space between the tabs 102 of the backplate 100 have a first diameter. In the first position, an unbiased position, the backplate 100 can have a curvilinear profile. In the second position, the space between the tabs 102 of the backplate 100 have a second diameter that is larger than the first diameter. The first diameter corresponds to the diameter of the ridge 204 of the neck portion 203. The second diameter is slightly larger than the diameter of the coaxial collar and neck portion 203. At 402, the neck portion 203 of the optical stem 202 is inserted in the space between the tabs 102 and the annular ring 101 of the backplate 100. At 402, the neck portion 203 is inserted until the ridge 204 in the neck portion 203 is adjacent the tabs 102. In some implementations, a sleeve such as sleeve 301 is inserted about the neck portion 203 and a donor corneal graft or corneal tissue is positioned about the neck portion 203, before the neck portion 203 is inserted in the space between the tabs 102. At 403, the appendages 103 are released so that the backplate 100 returns to the unbiased position. Upon release of the appendages at 403, the space between the tabs 102 of the backplate 100 return to the first diameter and the tabs 102 are engaged in the ridge 204.

Figure 5:
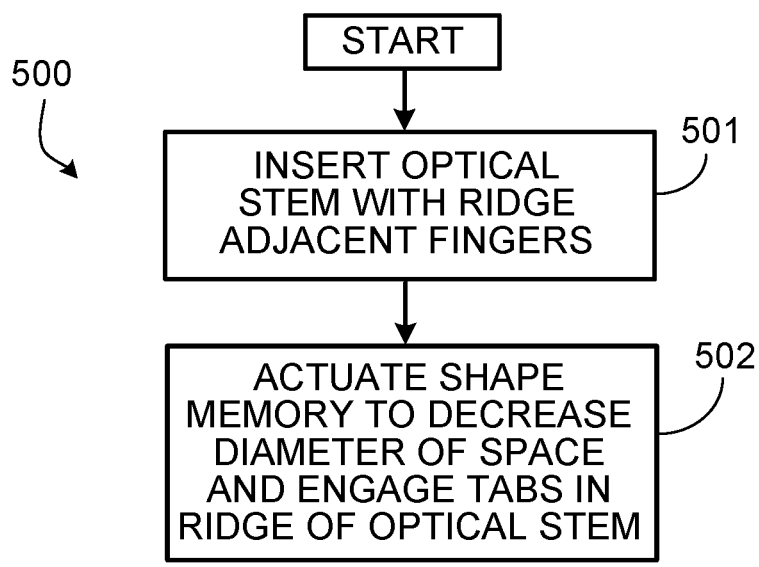
FIG. 5 is a flow diagram of another example of a method of forming a keratoprosthesis apparatus.
Figure 6A:
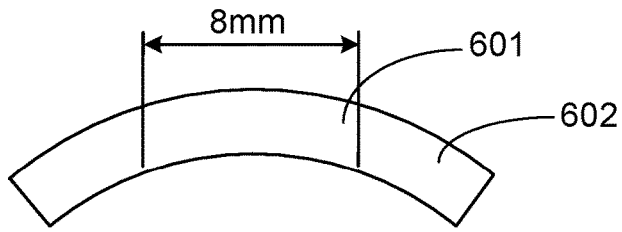
FIGS. 6A-6E are schematic diagrams that illustrate a process for implanting a keratoprosthesis apparatus.
Figure 6C:
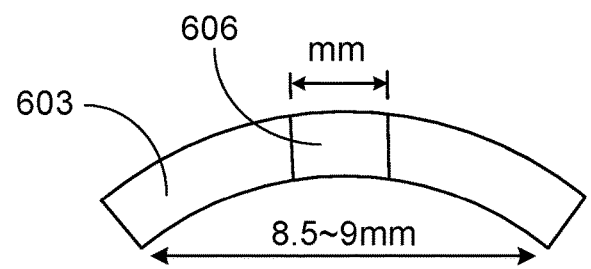
Figure 6B:
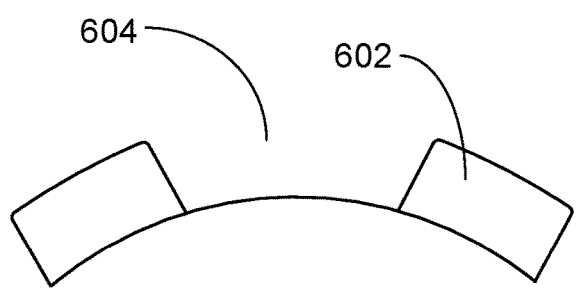
Figure 6D:
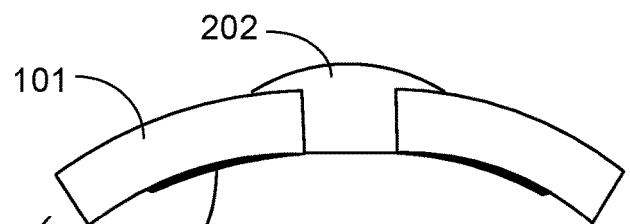
Figure 6E:
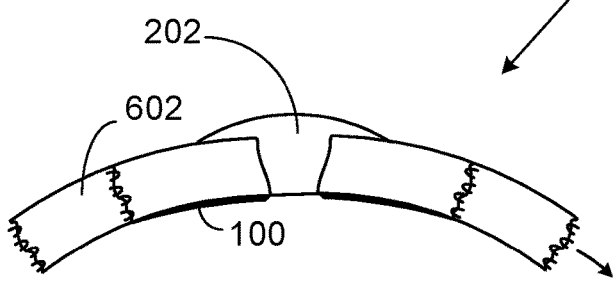

FIG. 5 is a flow diagram of another method of forming a keratoprosthesis apparatus. The keratoprosthesis apparatus formed by method 500 may be formed using a flexible backplate 100 composed at least in part, of a shape memory alloy. At 501, the neck portion 203 of the optical stem 202 is inserted in the space between the tabs 102 and the annular ring 101 of the backplate 100 until the ridge 204 in the neck portion 203 is adjacent the tabs 102. At 502, the shape memory material of the flexible backplate 100 is then actuated (either moved or released) so that the flexible backplate 100 moves to a second shape where the diameter between the tabs 102 is smaller than the diameter between the tabs 102 before actuation. During this actuation, the tabs 102 are engaged in the ridge 204. The shape memory material can be actuated via a change in temperature.

Methods of Implanting Keratoprosthesis Apparatuses

FIG. 6 illustrates a process for implanting a keratoprosthesis apparatus using a DALK technique. As shown in FIG. 6A, a section 601 (approximately 8 mm) of an anterior cornea 602 is removed. As shown in FIG. 6C, a donor cornea 603 configured to fit in the opening 604 (FIG. 6C) left of the anterior cornea 602 will receive a 3 mm central hole 606 and a PMMA optical stem 202 will be inserted and secured to the donor cornea 603 by the flexible titanium backplate 100 (FIG. 6D). As shown in FIG. 6E the PMMA stem 202 will be positioned on the surface of Descemet membrane, without penetrating into the anterior chamber. This surgical approach is not penetrating, thus minimizing the complications of a mesoimplant and simplifies the post-operative care. In addition, the flexible titanium backplate 100 can be implemented in regular Boston Keratoprosthesis implantation, providing corneal flexibility together with biomechanics support, thus resuming the physiological micro movement of the cornea.

Figure 7A:
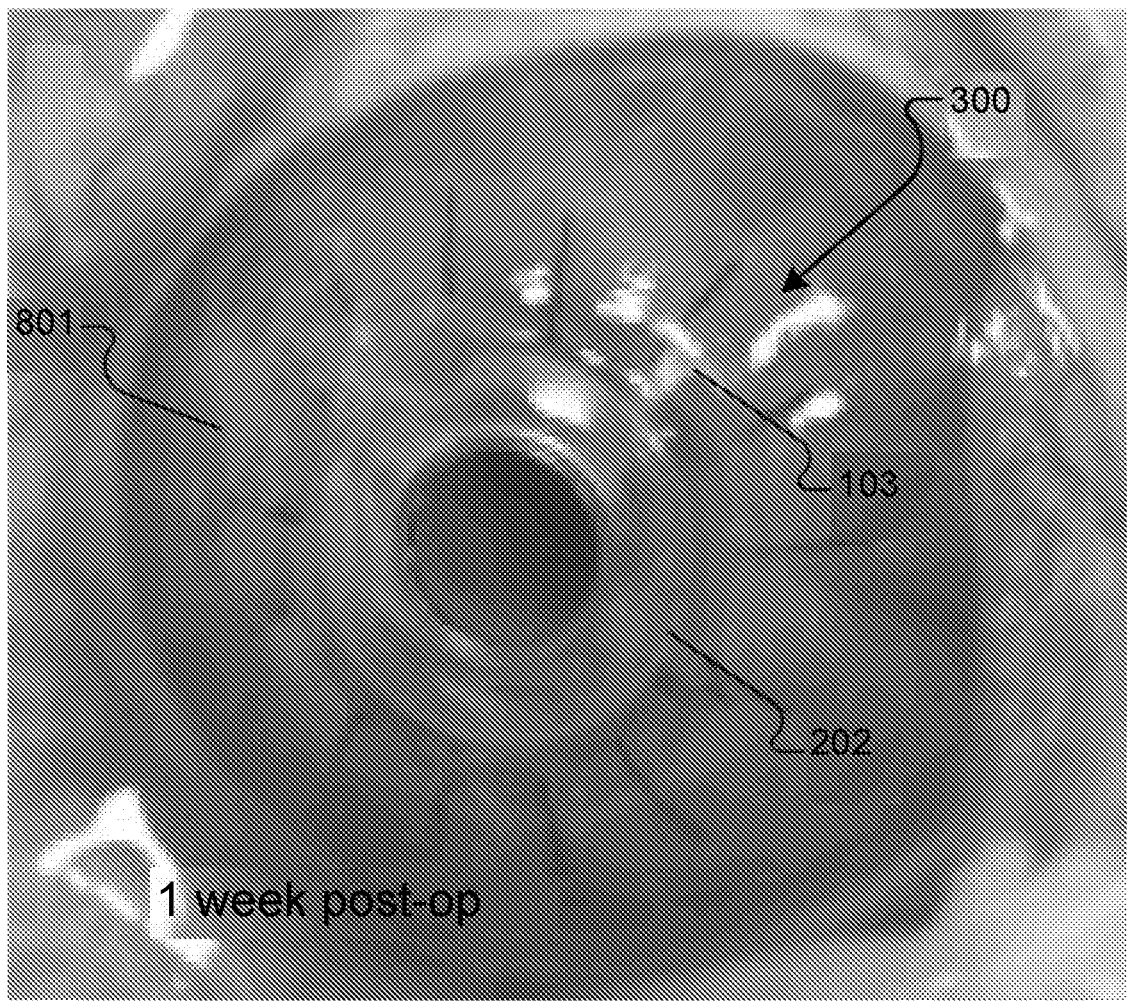
FIGS. 7A-7B are photographic representations of an implanted keratoprosthesis apparatus at 1 week and 10 months after implantation.
Figure 7B:
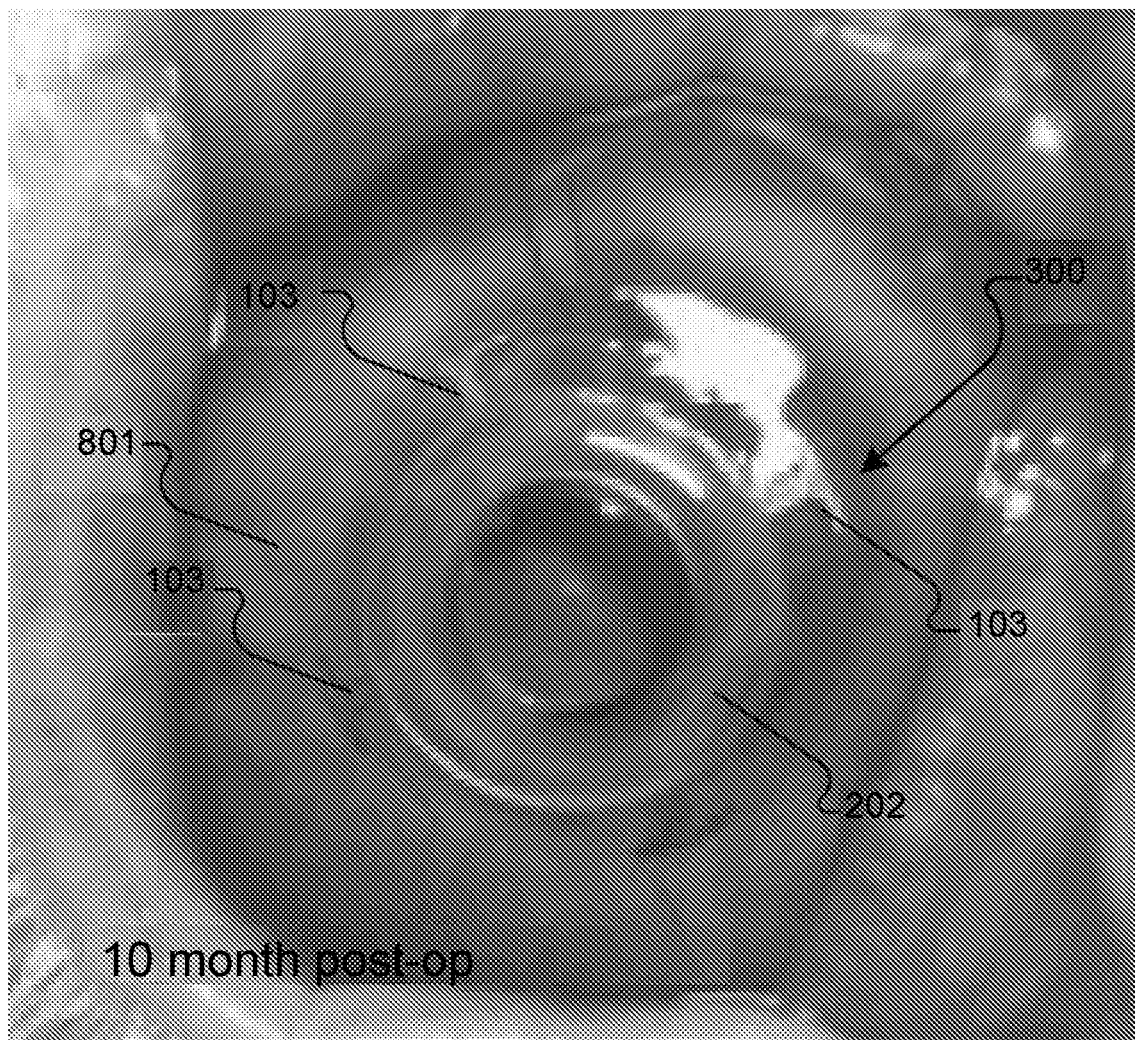
Figure 7C:
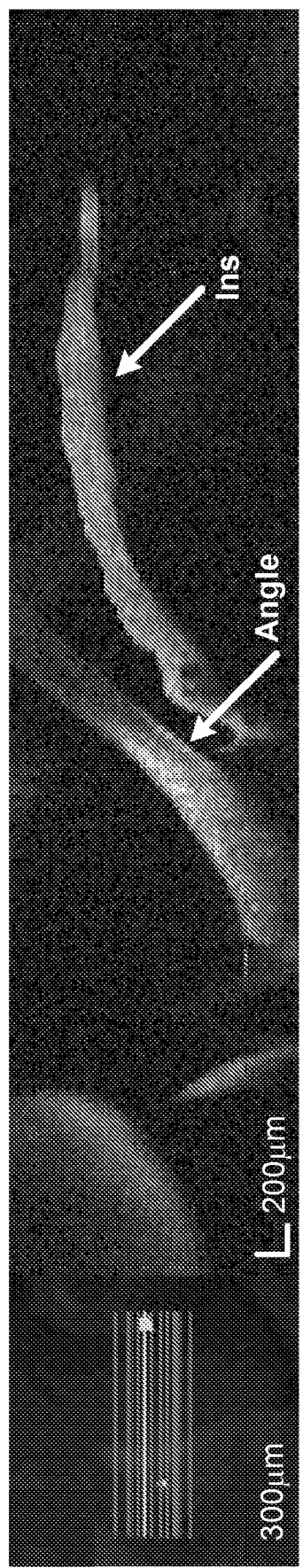
FIG. 7C is a photomicrographic representation of an eye in vivo using optical coherence tomography.

FIGS. 7A-7C show an implanted keratoprosthesis apparatus. The keratoprosthesis apparatus 300 is illustrated implanted in a rabbit eye 801 in FIG. 7A. The keratoprosthesis apparatus 300 was implanted in New Zealand white rabbits using DALK. An allograft donor cornea was used as a tissue carrier. FIG. 7A shows the implanted keratoprosthesis apparatus 300 one-week post-operation. FIG. 7B shows the implanted keratoprosthesis apparatus 300 ten months post-operation. The keratoprosthesis apparatus 300 was well tolerated by the eye 801 and caused minimal corneal inflammation and neovascularization.

FIG. 7C illustrates measurements taken in vivo via optical coherence tomography. At 10 months, the intraocular pressure (IOP) was normal (<18 mmHg) and similar to baseline (i.e., 17 mmHg), while the anterior chamber architecture was maintained. FIG. 7C shows that the corneal-iris angle (designated by "Angle" in the image) is open, allowing aqueous humor flow to the trabecular meshwork. The pupillary margin is positioned posteriorly to the cornea without signs of traction towards the graft junction.

The eye 801 developed some degree of retro-prosthetic membrane, which was loosely attached to the posterior surface of the optical stem 202. Successful removal of the retro-prosthetic membrane was performed through the clear cornea using a 30 G needle.

Figure 8:
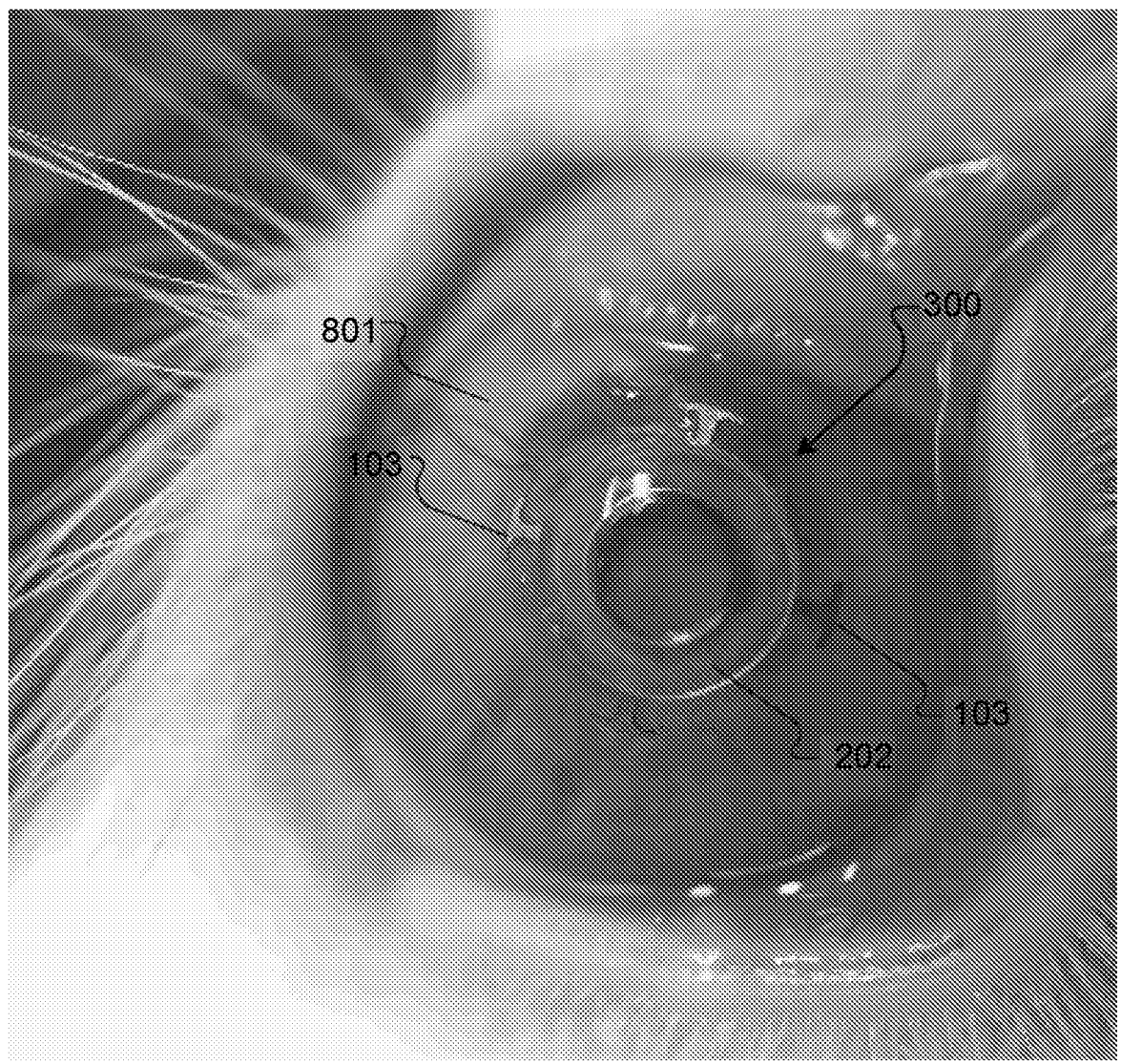
FIG. 8 is a photographic representation of an implant with the opacity between the lens and the Descemet's membrane removed using membranectomy.

FIG. 8 shows the keratoprosthesis after being implanted for 1 year in the rabbit eye. As demonstrated in FIG. 8, the allograft cornea appears transparent and well accepted by the host eye 801. The keratoprosthesis apparatus 300 is well retained, and the graft is griped tightly around the titanium sleeve 301 and optical stem 202. The anterior chamber architecture of eye 801 is intact with normal TOP (pre-op 17 mmHg, 1-year post-op 16 mmHg).

Figure 9:
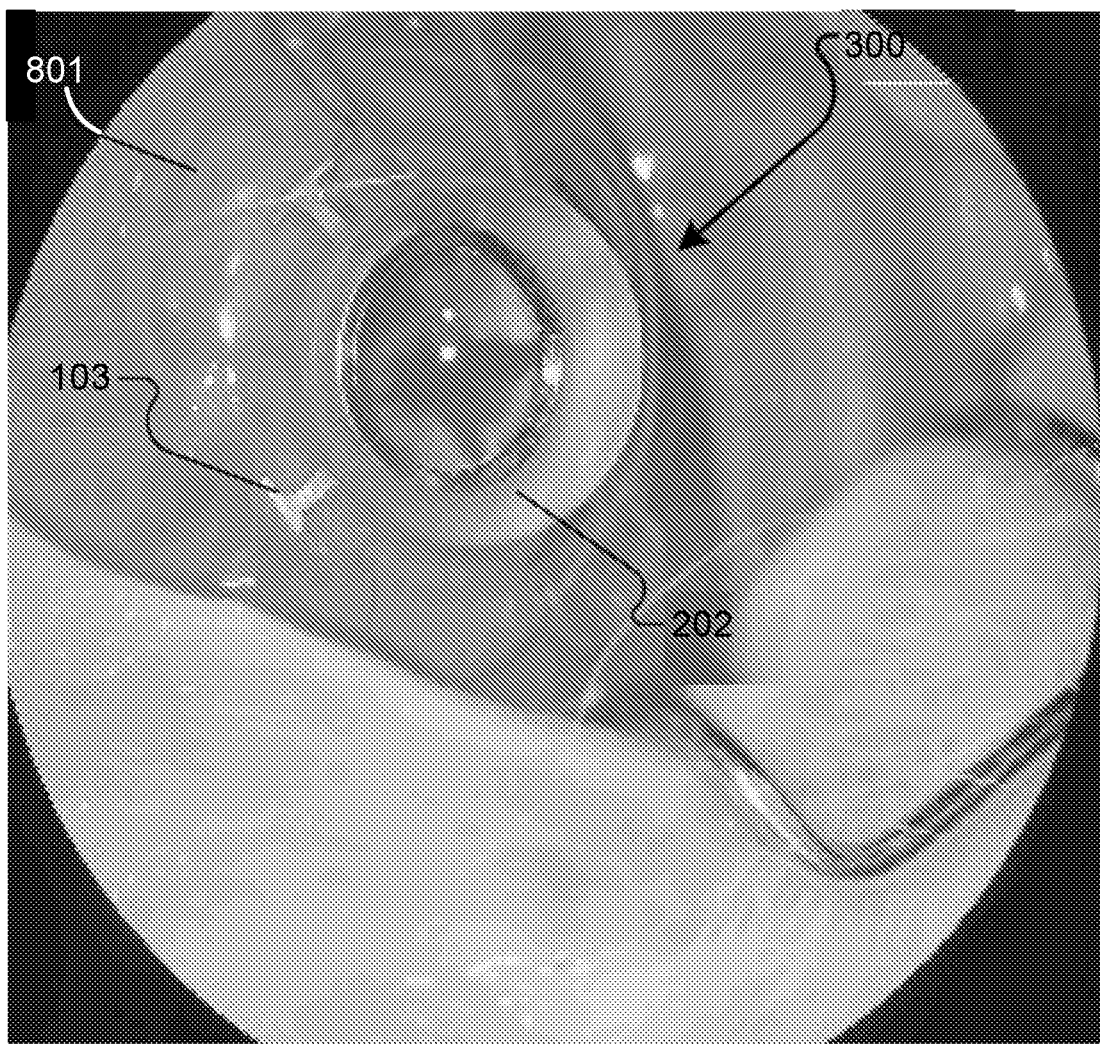
FIG. 9 is a photographic representation of the keratoprosthesis after being implanted for 1 year.

FIG. 9 shows the opening of the opaque Descemet's membrane behind the lens using membranotomy. Some opacity between the lens and the Descemet's membrane was formed after the surgery. The opacity in the membrane was removed using membranotomy using a 30 G needle that performed a crosscut of the Descemet's membrane. Preventative membranectomy can also be performed either immediately after implantation of the device, or at a later quiet stage. Alternatively, a YAG laser may be used to perform the membranotomy.

Figure 10:
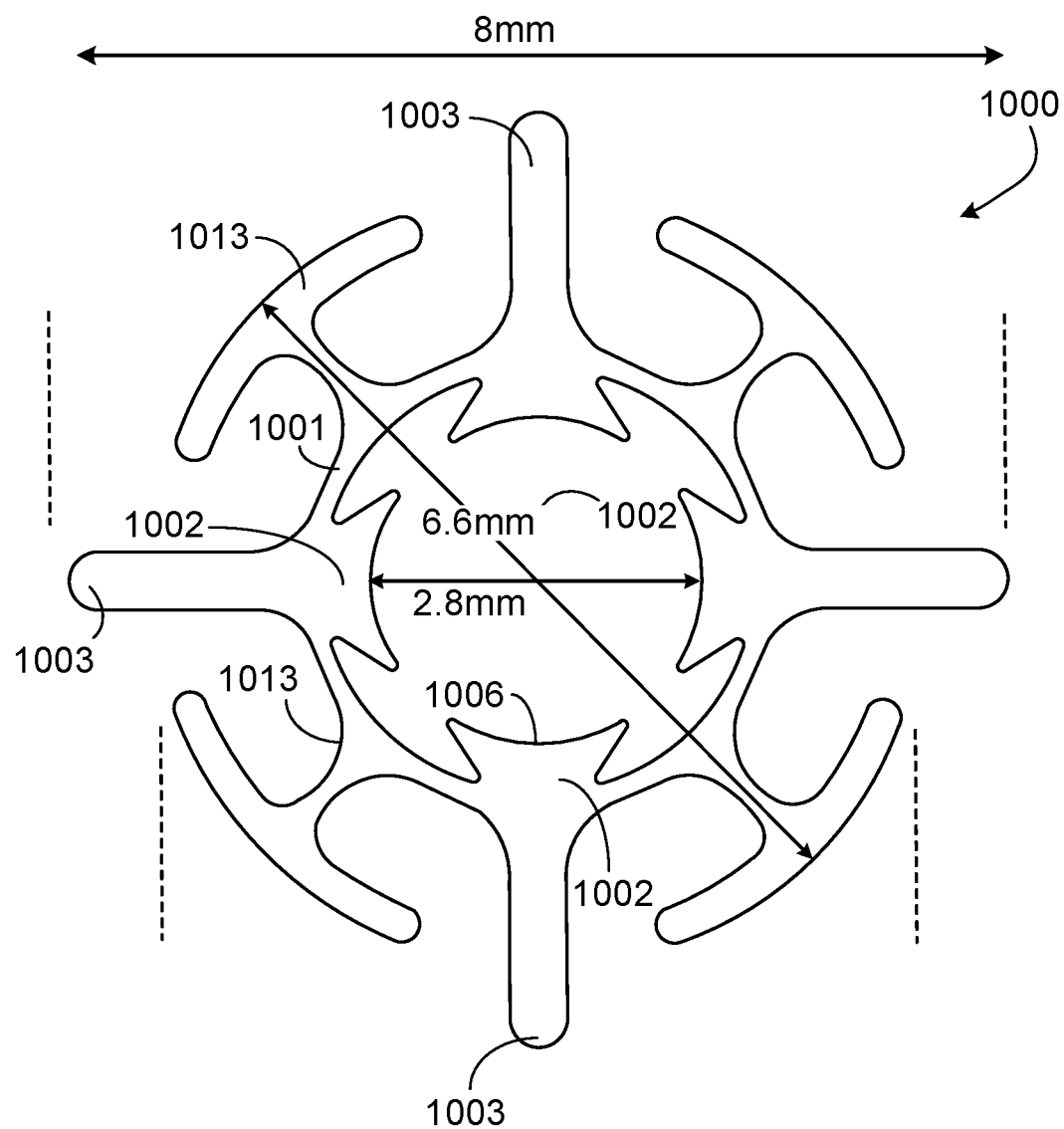
FIG. 10 is a schematic diagram that shows another example of a keratoprosthesis apparatus.

FIG. 10 shows another example of a flexible backplate for a keratoprosthesis apparatus. Flexible backplate 1000 includes a plurality of flexible appendages 1003 positioned about annular rim portion 1001. The flexible appendages 1003 provide support for a donor corneal graft or corneal tissue. A plurality of tabs 1002 having curved inner edges 1006 are positioned about the annular rim portion 1001 of the flexible backplate 1000. The inner edge 1006 of the tabs 1002 are configured for engagement with a round neck portion of an optical stem.

The flexible backplate 1000 also includes intermediate flexible appendages 1013 that provide extra tissue support for a donor corneal graft when a keratoprosthesis apparatus formed with the flexible backplate 1000 is implanted. The flexible backplate 1000 is generally composed of a titanium alloy, which can include, but is not limited to, a nickel titanium alloy and/or a nitinol titanium alloy. While the flexible backplate 1000 is illustrated with a nominal diameter of 2.8 mm between the curved edges 1006 of the tabs, a nominal diameter of 6.6 mm about the intermediate flexible appendages, and a nominal diameter of 8 mm about flexible appendages 1003, particular embodiments of the present invention include other diameters. The diameter and/or shape of the flexible backplate 1000 in any of the aforementioned regions can be independently tailored to a particular eye geometry, in accordance with certain embodiments of the present invention.

Figure 11:
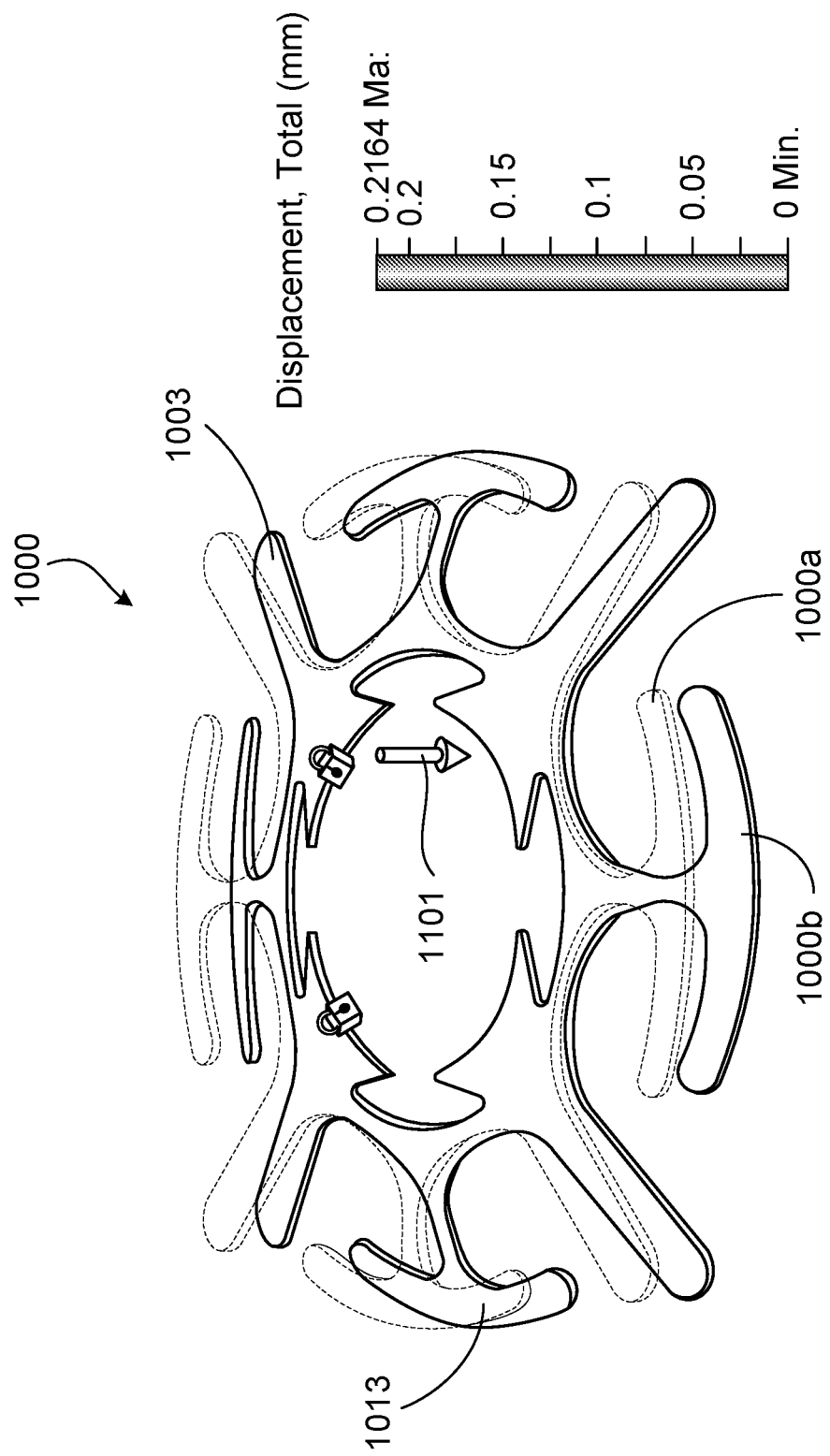
FIG. 11 is a schematic representation of a stress-strain simulation of the keratoprosthesis apparatus of FIG. 10.

FIG. 11 shows a stress-strain simulation of the keratoprosthesis apparatus of FIG. 10. FIG. 11 shows the variation in deformation of the flexible backplate 1000 under the application of deforming force 1101. The flexible backplate 1000 deforms from position 1000a to position 1000b, experiencing generally greater deformation as you move radially outward from the tabs 1002 to the flexible appendages 1003 and 1013. For example, the flexible appendages 1003 and 1013 experiences the greatest amount of strain at their outermost edge. In view of the radial position of the appendages, they have a significant amount of flexibility.

Embodiments of the present keratoprosthesis described herein can be implanted in different ways. In some implementations, the eye of the patient will undergo anterior lamellar keratoplasty, manual or femtosecond laser assisted. The excised corneal tissue (approx. 8 mm diameter) will be trephined centrally (approximately 3 mm diameter). An optical stem, such as the optical stem 202, will be inserted into the trephined tissue and secured with a flexible titanium backplate, such as flexible backplate 100. The assembled corneal tissue, optical stem, and flexible backplate will then be placed back on top of the Descemet membrane of the eye of a patient, and sutured around with interrupted or running suture (similar to penetrating keratoplasty).

In other implementations, the excised corneal tissue is discarded and a corneal donor graft is used instead, as described above (with or without the Descemet's membrane). An optical stem, such as the optical stem 202, will be inserted into the donor graft and secured with a flexible titanium backplate, such as flexible backplate 100. The assembled corneal tissue, optical stem, and flexible backplate will then be placed on top of the Descemet membrane of the eye of a patient and sutured, as previously described.

In other implementations, an eye of a patient will undergo a standard penetrating keratoplasty (full thickness). A deep anterior lamellar keratoplasty will then be performed on a donor corneal tissue. The anterior corneal donor tissue will be trephined and an optical stem, such as the optical stem 202, will be fitted and secured with a flexible titanium backplate, such as flexible backplate 100. The assembled graft, optical stem, and flexible backplate will then be placed on the donor's corneal bed and sutured as previously described. A larger diameter trephine will be used cut the donor tissue with the assembled optical stem, and flexible backplate. The tissue will then be placed and sutured in the eye of a patient, using standard penetrating keratoplasty procedures.

In some other implementations, the optical stem 202, will be fitted and secured with the flexible backplate 100 and will be implanted in the eye of a patient as performed traditionally with the Boston keratoprosthesis (i.e., a full thickness penetrating keratoplasty will be performed on the patient's eye and a donor corneal graft (full thickness) will undergo central trephination and fitting of the flexible backplate 100 (the tissue may or may not include the Descemet membrane of the donor). The assembled donor corneal graft and flexible backplate 100 will then be sutured to the patient's eye as full thickness penetrating keratoplasty.

The surgical implantation implementations disclosed herein may also be performed using engineered corneas or constructs, made of human or animal collagen, polymer, or other synthetic or biologic materials in accordance with embodiments of the present invention. In addition, donor xenograft tissue from animal or other parts of the human tissue can be used as tissue carriers to perform the above surgical implantation implementations.

Various processes and logic flows described in this specification, such as actuation of a shape memory alloy of a flexible backplate, can be performed by one or more programmable processors executing one or more computer programs to perform actions by operating on input data and generating output. The processes and logic flows can also be performed by, and apparatus can also be implemented as, special purpose logic circuitry, e.g., a FPGA (field programmable gate array) or an ASIC (application specific integrated circuit).

OTHER EMBODIMENTS

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub combination. Moreover, although features may be described above as acting in certain combinations and even initially claimed as such, one or more features from a claimed combination can in some cases be excised from the combination, and the claimed combination may be directed to a sub combination or variation of a sub combination.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub combination. Moreover, although features may be described above as acting in certain combinations and even initially claimed as such, one or more features from a claimed combination can in some cases be excised from the combination, and the claimed combination may be directed to a sub combination or variation of a sub combination.

The orientation of various elements may differ according to other exemplary implementations, and such variations are encompassed by the present disclosure. Features of the disclosed implementations can be incorporated into other disclosed implementations.

While various inventive implementations have been described and illustrated herein, a variety of other means and/or structures for performing the function and/or obtaining the results and/or one or more of the advantages described herein are, and each of such variations and/or modifications is, deemed to be within the scope of the inventive implementations described herein. The foregoing implementations are presented by way of example only and that, within the scope of the appended claims and equivalents thereto, inventive implementations may be practiced otherwise than as specifically described and claimed. Inventive implementations of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, the technology described herein may be embodied as a method, of which at least one example has been provided. The acts performed as part of the method may be ordered in any suitable way. Accordingly, implementations may be constructed in which acts are performed in an order different than illustrated, which may include performing some acts simultaneously, even though shown as sequential acts in illustrative implementations.

The claims should not be read as limited to the described order or elements unless stated to that effect. It should be understood that various changes in form and detail may be made by one of ordinary skill in the art without departing from the spirit and scope of the appended claims. All implementations that come within the spirit and scope of the following claims and equivalents thereto are claimed.

What is claimed is:

1. A keratoprosthesis apparatus comprising:
   a circular backplate composed, at least in part, of a titanium alloy, wherein the circular backplate includes an annular rim portion having a central aperture extending therethrough;
   a first plurality of tabs positioned along the annular rim portion and extending radially inwardly into the aperture; and
   a plurality of flexible appendages extending radially outwardly from the annular rim portion and positioned along the annular rim portion at locations corresponding to the first plurality of tabs, wherein the plurality of flexible appendages is configured to provide leverage to pivot the first plurality of tabs outwardly.

2. The keratoprosthesis apparatus of claim 1, wherein the titanium alloy includes a super elastic alloy.

3. The keratoprosthesis apparatus of claim 1, wherein the titanium alloy comprises a shape memory alloy.

4. The keratoprosthesis apparatus of claim 3, wherein the titanium alloy comprises a titanium nickel alloy.

5. The keratoprosthesis apparatus of claim 1, further comprising an optical stem including a curvilinear crown portion and a neck portion extending from the curvilinear crown portion, wherein the neck portion comprises an annular ridge having a smaller diameter than a remainder of the neck portion, and wherein the circular backplate is coupled to the optical stem via engagement of the plurality of tabs in the ridge of the neck portion of the optical stem.

6. The keratoprosthesis apparatus of claim 5, further comprising a coaxial sleeve positioned about the neck portion of the optical stem, wherein the coaxial sleeve includes a sleeve ridge corresponding to the annular ridge, and wherein the circular backplate is coupled to the optical stem via engagement of the plurality of tabs in the sleeve ridge.

7. The keratoprosthesis apparatus of claim 6, wherein the sleeve comprises titanium.

8. The keratoprosthesis apparatus of claim 1, wherein one or more tabs in the first plurality of tabs include a curved edge.

9. The keratoprosthesis apparatus of claim 1, wherein the circular backplate is configured in a curvilinear profile.

10. The keratoprosthesis apparatus of claim 1, further comprising a second plurality of appendages extending radially outwardly from the annular rim portion and positioned along the annular rim portion at locations intermediate to the first plurality of tabs.

11. A method of assembling a keratoprosthesis apparatus, the method comprising:
  obtaining a circular backplate having a plurality of tabs positioned along and extending radially inwardly from an annular rim portion of the circular backplate, the plurality of tabs defining a space between them;
  moving the plurality of tabs by flexing a plurality of flexible appendages extending radially outwardly from the annular rim portion and positioned along the annular rim portion at locations corresponding to the plurality of tabs, whereby the plurality of tabs pivot about the annular rim portion so as to increase a diameter of a space between the plurality of tabs;
  inserting a neck portion of an optical stem including a curvilinear crown portion into the space between the plurality of tabs so as to position an annular ridge in the neck portion having a smaller diameter than a remainder of the neck portion adjacent to the plurality of tabs; and
  releasing the plurality of flexible appendages to reduce the diameter of the space between the plurality of tabs to engage the plurality of tabs in the ridge.

12. The method of claim 11, further comprising inserting a sleeve about the neck portion of the optical stem so that the sleeve is positioned on the neck portion between the circular backplate and the neck portion of the optical stem.

13. A method of assembling a keratoprosthesis apparatus, the method comprising:
  inserting a neck portion of an optical stem including a curvilinear crown portion into a space between a plurality of tabs positioned along and extending radially inwardly from an annular rim portion of a circular backplate composed of a shape memory alloy and having a plurality of flexible appendages extending radially outwardly from the annular rim portion and positioned along the annular rim portion so as to position an annular ridge having a smaller diameter than the neck portion adjacent the plurality of tabs; and
  inwardly flexing the plurality of tabs to reduce a diameter of the space between the plurality of tabs by actuating the shape memory alloy to engage the plurality of tabs in the ridge.

14. The method of claim 13, wherein causing the plurality of tabs to flex inwardly by actuating the shape memory alloy includes changing the temperature of the circular backplate.

15. A keratoprosthesis apparatus comprising:
  a circular backplate composed, at least in part, of a titanium alloy, wherein the circular backplate includes an annular rim portion having a central aperture extending therethrough;
  a plurality of tabs positioned along the annular rim portion and extending radially inwardly into the aperture;
  a plurality of flexible appendages extending radially outwardly from the annular rim portion and positioned along the annular rim portion; and
  an optical stem including a curvilinear crown portion and a neck portion extending from the curvilinear crown portion, wherein the neck portion comprises an annular ridge having a smaller diameter than a remainder of the neck portion, and wherein the circular backplate is coupled to the optical stem via engagement of the plurality of tabs in the ridge of the neck portion of the optical stem.

16. The keratoprosthesis apparatus of claim 15, further comprising bilateral extensions extending from a radially outer end of a flexible appendage in the plurality of flexible appendages.

17. The keratoprosthesis apparatus of claim 16, wherein the bilaterally extensions are curvilinear.

18. The keratoprosthesis apparatus of claim 17, wherein the plurality of tabs include a curved edge configured to engage the annular ridge in the neck portion.

* * * * *

UNITED STATES PATENT AND TRADEMARK OFFICE
CERTIFICATE OF CORRECTION

PATENT NO. : 11,026,778 B2
APPLICATION NO. : 16/327029
DATED : June 8, 2021
INVENTOR(S) : Eleftherios Ilios Paschalis Page 1 of 1

It is certified that error appears in the above-identified patent and that said Letters Patent is hereby corrected as shown below:

In the Claims

In Column 12, Line 20, Claim 13, after "adjacent" insert -- to --

Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*